United States Patent
Bestel-Corre et al.

(10) Patent No.: US 8,088,620 B2
(45) Date of Patent: Jan. 3, 2012

(54) OPTIMISED MICRO-ORGANISM STRAINS FOR NADPH-CONSUMING BIOSYNTHETIC PATHWAYS

(75) Inventors: Gwénaëlle Bestel-Corre, Saint Beauzire (FR); Cédric Boisart, Chamallières (FR); Michel Chateau, Riom (FR); Benjamin Gonzalez, Riom (FR); Philippe Soucaille, Deyme (FR); Rainer Figge, Riom (FR); Olivier Zink, Mulhouse (FR)

(73) Assignee: Metabolic Explorer, Saint Beauzire (FR)

( * ) Notice: Subject to any disclaimer, the term of this patent is extended or adjusted under 35 U.S.C. 154(b) by 1280 days.

(21) Appl. No.: 10/577,084

(22) PCT Filed: Nov. 5, 2004

(86) PCT No.: PCT/FR2004/002848
§ 371 (c)(1),
(2), (4) Date: May 18, 2006

(87) PCT Pub. No.: WO2005/047498
PCT Pub. Date: May 26, 2005

(65) Prior Publication Data
US 2007/0087403 A1    Apr. 19, 2007

(30) Foreign Application Priority Data
Nov. 6, 2003 (FR) ...................................... 03 13056

(51) Int. Cl.
C12N 15/00 (2006.01)
C12N 1/21 (2006.01)
C12N 1/16 (2006.01)
C12P 13/04 (2006.01)
C12P 1/00 (2006.01)

(52) U.S. Cl. .......... 435/440; 435/106; 435/132; 435/41; 435/252.1; 435/252.2; 435/252.3; 435/252.7; 435/252.8; 435/252.5; 435/256.3; 435/255.2; 435/255.5

(58) Field of Classification Search ....................... None
See application file for complete search history.

(56) References Cited

OTHER PUBLICATIONS

International Application Publication No. WO98/02552, Jan. 22, 1998.
European Patent Application Publication No. EP170376, Jan. 9, 2002.
Bersova et al. (2001) *J. Bacteriology* 183:6869-6874.
Boles et al. (1993) *Eur. J. Biochem.* 217:469-477.
Calhoun et al. (1993) *J. Bacteriology* 175:3013-3019.
Frerichs-Deeken et al. (2003) *Eur. J. Biochem.* 270:1567-1577.
Kervinen et al. (2004) *Biochemistry* 43:773-781.
Marx et al. (2003) *Journal of Biotechnology* 104:185-197.
Molenaar et al. (2000) *J. Bacteriology* 182:6884-6891.
Morita et al. (2003) *J. Biol. Chem.* 278-15608-15614.
Nyunoya et al. (1984) *Can. J. Microbiol.* 30-45-51.
Pieulle et al. (2000) *FEBS Letters* 487-272-276.
Sauer et al. (2004) *J. Biol. Chem.* 279:6613-6619.
Yamaguchi et al. (1995) *J. Biol. Chem.* 270:16653-16659.
Kabir et al., "Fermentation Characteristics and Protein Expression Patterns in a Recombinant *Escherichia coli* Lacking *Phosphogiucose isomerase* for Poly (3-Hydroxybutyrate) Production"—Applied Microbiology Biotechnology, 2003.
Althage et al., "Functional Split and Crosslinking of the Membrane Domain of the 3 Subunit of Proton-Translocating Transhydrogenase From *Escherichia coli*" Biochemistry, 2003.
PCT International Search Report, May 2, 2005.

*Primary Examiner* — Nancy Vogel
(74) *Attorney, Agent, or Firm* — Baker Donelson Bearman, Caldwell & Berkowitz, PC

(57) ABSTRACT

The invention relates to optimised micro-organism strains for the biotransformation production of molecules having NADPH-consuming biosynthetic pathways. The inventive strains can be used in NADPH-consuming biotransformation methods. Said strains are characterized in that one or more NADPH-oxidizing activities are limited.

13 Claims, No Drawings

SEQUENCE LISTING

<160> NUMBER OF SEQ ID NOS: 38

<210> SEQ ID NO 1
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 1
ggtgcgcgcg tcgcagttat cgagcgttat caaaatgttg gcggcggttg cacccactgg    60
ggcaccatcc cgtcgaaagc catatgaata tcctccttag                         100

<210> SEQ ID NO 2
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 2
cccagaatct cttttgtttc ccgatggaac aaaattttca gcgtgcccac gttcatgccg    60
acgatttgtg cgcgtgccag tgtaggctgg agctgcttcg                         100

<210> SEQ ID NO 3
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 3
ggccgctcag gatatagcca gataaatgac                                     30

<210> SEQ ID NO 4
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 4
gcgggatcac tttactgcca gcgctggctg                                     30

<210> SEQ ID NO 5
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 5 ggtgcccgg aagtacttca agccgtagag ttcactcctg ccgatccggc ggagaatgaa     60
atccaggtcg aaaataaagc catatgaata tcctccttag                         100

<210> SEQ ID NO 6
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 6

```
cgcccggctt tccagaatct catgcgcacg ctgcgcatcc ttcagcggat atttctgctg      60
ctcggcgaca tcgaccttaa tgtaggctgg agctgcttcg                          100
```

<210> SEQ ID NO 7
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 7

```
cgcccaacac cgactgctcc gcttcgatcg                                      30
```

<210> SEQ ID NO 8
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 8

```
cagcgttatg accgctggcg ttactaaggg                                      30
```

<210> SEQ ID NO 9
<211> LENGTH: 43
<212> TYPE: DNA
<213> ORGANISM: artificial sequence
<220> FEATURE:
<223> OTHER INFORMATION: Other information : synthetic oligonucleotide

<400> SEQUENCE: 9

```
acgtacgtgg catatgtcag ttttcgtttc aggtgctaac ggg                       43
```

<210> SEQ ID NO 10
<211> LENGTH: 44
<212> TYPE: DNA
<213> ORGANISM: artificial sequence
<220> FEATURE:
<223> OTHER INFORMATION: Other information : synthetic oligonucleotide

<400> SEQUENCE: 10

```
acgtacctgc agttatattc tgccctcaaa ttttaaaatt tggg                      44
```

<210> SEQ ID NO 11
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 11

```
ccaacgcaga ccgctgcctg gcaggcacta cagaaacact tcgatgaaat gaaagacgtt      60
acgatcgccg atcttttgc tgtaggctgg agctgcttcg                           100
```

<210> SEQ ID NO 12
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 12

```
gcgccacgct ttatagcggt taatcagacc attggtcgag ctatcgtggc tgctgatttc      60
tttatcatct ttcagctctg catatgaata tcctccttag                          100
```

```
<210> SEQ ID NO 13
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 13
gcggggcggt tgtcaacgat ggggtcatgc                                       30

<210> SEQ ID NO 14
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 14
cggtatgatt tccgttaaat tacagacaag                                       30

<210> SEQ ID NO 15
<211> LENGTH: 102
<212> TYPE: DNA
<213> ORGANISM: artificial sequence
<220> FEATURE:
<223> OTHER INFORMATION: Other information : synthetic oligonucleotide

<400> SEQUENCE: 15
cgcgcgagac tcgctctgct tatctcgccc ggatagaaca agcgaaaact tcgaccgttc      60
atcgttcgca gttggcatgc ggtgtaggct ggagctgctt cg                        102

<210> SEQ ID NO 16
<211> LENGTH: 98
<212> TYPE: DNA
<213> ORGANISM: artificial sequence
      <213>  artificial sequence
<220> FEATURE:
<220> FEATURE:
<223> OTHER INFORMATION: Other information : synthetic oligonucleotide

<400> SEQUENCE: 16
cgcaaggcgc tgaataattc acgtcctgtt cccacgcgtg acgcgctcag gtcaggaatg      60
tgcggttcgc gagcagccca tatgaatatc ctccttag                             98

<210> SEQ ID NO 17
<211> LENGTH: 29
<212> TYPE: DNA
<213> ORGANISM: artificial sequence
<220> FEATURE:
<223> OTHER INFORMATION: Other information : synthetic oligonucleotide

<400> SEQUENCE: 17
gggtagactc cattactgag gcgtgggcg                                        29

<210> SEQ ID NO 18
<211> LENGTH: 24
<212> TYPE: DNA
<213> ORGANISM: artificial sequence
<220> FEATURE:
<223> OTHER INFORMATION: Other information : synthetic oligonucleotide

<400> SEQUENCE: 18
ccccggaatc agaggaatag tccc                                             24

<210> SEQ ID NO 19
```

<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 19
ggtgtgttga caagcggcgg tgatgcgcca ggcatgaacg ccgcaattcg cggggttgtt         60
cgttctgcgc tgacagaagg tgtaggctgg agctgcttcg                             100

<210> SEQ ID NO 20
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 20
ttcgcgcagt ccagccagtc acctttgaac ggacgcttca tgttttcgat agcgtcgatg         60
atgtcgtggt gaaccagctg catatgaata tcctccttag                             100

<210> SEQ ID NO 21
<211> LENGTH: 27
<212> TYPE: DNA
<213> ORGANISM: artificial sequence
<220> FEATURE:
<223> OTHER INFORMATION: Other information : synthetic oligonucleotide

<400> SEQUENCE: 21
cgcacgcggc agtcagggcc gacccgc                                            27

<210> SEQ ID NO 22
<211> LENGTH: 27
<212> TYPE: DNA
<213> ORGANISM: artificial sequence
<220> FEATURE:
<223> OTHER INFORMATION: Other information : synthetic oligonucleotide

<400> SEQUENCE: 22
ccctacgccc cacttgttca tcgcccg                                            27

<210> SEQ ID NO 23
<211> LENGTH: 99
<212> TYPE: DNA
<213> ORGANISM: artificial sequence
<220> FEATURE:
<223> OTHER INFORMATION: Other information : synthetic oligonucleotide

<400> SEQUENCE: 23
gcgccctctc tcgatagcgc aacaattacc ccgcaaattt atcccgaagg aaaactgcgc         60
tgtaccgcac cggtgttcgt gtaggctgga gctgcttcg                               99

<210> SEQ ID NO 24
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 24
gcgggaaagg taagcgtaaa ttttttgcgt atcgtcatgg gagcacagac gtgttccctg         60
attgagtgtg gctgcactcc catatgaata tcctccttag                             100

<210> SEQ ID NO 25

```
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 25
tggcaggatc atccatgaca gtaaaaacgg                                        30

<210> SEQ ID NO 26
<211> LENGTH: 26
<212> TYPE: DNA
<213> ORGANISM: artificial sequence
<220> FEATURE:
<223> OTHER INFORMATION: Other information : synthetic oligonucleotide

<400> SEQUENCE: 26
gccggttgca ctttgggtaa gccccg                                            26

<210> SEQ ID NO 27
<211> LENGTH: 43
<212> TYPE: DNA
<213> ORGANISM: artificial sequence
<220> FEATURE:
<223> OTHER INFORMATION: Other information : synthetic oligonucleotide

<400> SEQUENCE: 27
acgtacgtcc cccgggaaaa atgtcagttt tcgtttcagg tgc                         43

<210> SEQ ID NO 28
<211> LENGTH: 44
<212> TYPE: DNA
<213> ORGANISM: artificial sequence
<220> FEATURE:
<223> OTHER INFORMATION: Other information : synthetic oligonucleotide

<400> SEQUENCE: 28
acgtacgggc ccttatattc tgccctcaaa ttttaaaatt tggg                        44

<210> SEQ ID NO 29
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 29
ccaacgcaga ccgctgcctg gcaggcacta cagaaacact tcgatgaaat gaaagacgtt       60
acgatcgccg atcttttgc tgtaggctgg agctgcttcg                             100

<210> SEQ ID NO 30
<211> LENGTH: 100
<212> TYPE: DNA
<213> ORGANISM: artificial sequence
<220> FEATURE:
<223> OTHER INFORMATION: Other information : synthetic oligonucleotide

<400> SEQUENCE: 30
gcgccacgct ttatagcggt taatcagacc attggtcgag ctatcgtggc tgctgatttc       60
tttatcatct ttcagctctg catatgaata tcctccttag                            100

<210> SEQ ID NO 31
<211> LENGTH: 30
<212> TYPE: DNA
<213> ORGANISM: artificial sequence
<220> FEATURE:
```

<223> OTHER INFORMATION: Other information : synthetic oligonucleotide

<400> SEQUENCE: 31
gcggggcggt tgtcaacgat ggggtcatgc                                              30

<210> SEQ ID NO 32
<211> LENGTH: 30
<212> TYPE: DNA
<213> ORGANISM: artificial sequence
<220> FEATURE:
<223> OTHER INFORMATION: Other information : synthetic oligonucleotide

<400> SEQUENCE: 32
cggtatgatt tccgttaaat tacagacaag                                              30

<210> SEQ ID NO 33
<211> LENGTH: 82
<212> TYPE: DNA
<213> ORGANISM: artificial sequence
<220> FEATURE:
<223> OTHER INFORMATION: Other information : synthetic oligonucleotide

<400> SEQUENCE: 33
atgcaatctc aagattcatg ctacggtgtt gcattcagat ctatcatcac aaatgatgaa            60
aagcttcgta cgctgcaggt cg                                                      82

<210> SEQ ID NO 34
<211> LENGTH: 83
<212> TYPE: DNA
<213> ORGANISM: artificial sequence
<220> FEATURE:
<223> OTHER INFORMATION: Other information : synthetic oligonucleotide

<400> SEQUENCE: 34
tttgttttca gcggctaaag cggctacctc agctctcaac tttaatctac cggacaggat            60
gggccactag tggatctgat atc                                                     83

<210> SEQ ID NO 35
<211> LENGTH: 22
<212> TYPE: DNA
<213> ORGANISM: artificial sequence
<220> FEATURE:
<223> OTHER INFORMATION: Other information : synthetic oligonucleotide

<400> SEQUENCE: 35
gctttcttag aagctaccctc cg                                                     22

<210> SEQ ID NO 36
<211> LENGTH: 22
<212> TYPE: DNA
<213> ORGANISM: artificial sequence
<220> FEATURE:
<223> OTHER INFORMATION: Other information : synthetic oligonucleotide

<400> SEQUENCE: 36
gaaccgacaa gaccaacaat gg                                                      22

<210> SEQ ID NO 37
<211> LENGTH: 20
<212> TYPE: DNA
<213> ORGANISM: artificial sequence
<220> FEATURE:
<223> OTHER INFORMATION: Other information : synthetic oligonucleotide

<400> SEQUENCE: 37

```
cagttgtaca ctttggaccc                                              20

<210> SEQ ID NO 38
<211> LENGTH: 22
<212> TYPE: DNA
<213> ORGANISM: artificial sequence
<220> FEATURE:
<223> OTHER INFORMATION: Other information : synthetic oligonucleotide

<400> SEQUENCE: 38
gatcagcacc agtcaaagaa cc                                           22
```

OPTIMISED MICRO-ORGANISM STRAINS FOR NADPH-CONSUMING BIOSYNTHETIC PATHWAYS

NADP (nicotinamide adenine dinucleotide phosphate), in its reduced form NADPH, takes part in intracellular redox reactions involving enzymes with dehydrogenase or reductase activities.

The present invention concerns strains of microorganisms optimized for the production, by biotransformation, of substances with NADPH-consuming biosynthesis routes. The strains according to the invention can be used in NADPH-consuming biotransformation processes. The strains defined according to the invention can be prokaryotic or eukaryotic. In a preferred embodiment, the prokaryotic strain is a strain of *Escherichia coli*. In a further embodiment the eukaryotic strain is a strain of *Saccharomyces*, in particular *S. cerevisiae*.

The present invention also concerns a process for the preparation of substances by biotransformation, through growth in an appropriate medium of a strain optimized according to the invention, which optimized strain also includes the genetic elements necessary for the preparation of such substances.

Biotransformation processes have been developed to allow the production of required substances in large quantities and at low cost, while at the same time making profitable use of various industrial or agricultural by-products.

There are two main approaches for producing substances of interest by in vivo biotransformation:
1) Fermentation, whereby a substance is produced by a microorganism from a simple carbon source (e.g. WO0102547, which describes the production of lysine by fermentation of *C. glutamicum* in the presence of glucose).
2) Bioconversion by a microorganism of a given co-substrate into a substance of interest (e.g. WO0012745, which describes the production of derivatives of R-piperidine, and WO0068397, which describes the production of tagatose). The co-substrate is not assimilated and is distinct from the carbon source, which is used solely to produce the biomass and the NADPH necessary for bioconversion.

The improvement of a biotransformation process can concern various factors such as temperature, oxygenation, medium composition, recovery process, etc. It can also be possible to modify a microorganism so as to increase the production and/or excretion of a substance of interest.

In a fermentation approach, for example, the biosynthesis route can be improved, for example, by modifying gene regulation or by modifying genes to change the characteristics of the enzymes involved, or by optimizing the regeneration of cofactors.

In a bioconversion approach the emphasis will be placed on reducing the formation of by-products and optimizing the regeneration of the cofactors involved in the bioconversion step or steps.

Among the cofactors involved in the biotransformations, NADPH is important in particular for the production of amino acids (e.g. arginine, proline, isoleucine, methionine, lysine), vitamins (e.g. pantothenate, phylloquinone, tocopherol), aromatics (e.g. WO9401564), polyols (e.g. xylitol), polyamines (e.g. spermidine), hydroxyesters (e.g. ethyl-4-chloro-3-hydroxybutyrate) and other high added-value substances.

The present invention concerns a strain of microorganisms optimized for the production of substances with NADPH-consuming biosynthesis routes.

Instead of seeking to optimize the NADPH/NADP$^+$ ratio in the microorganism for each biotransformation, the inventors chose to produce modified microorganisms in order to obtain different NADPH/NADP$^+$ ratios, which modified microorganisms were then used to carry out NADPH-consuming biotransformations.

According to the invention a strain of microorganism is taken to mean a set of microorganisms of the same species comprising at least one microorganism of that species. Thus the characteristics described for the strain apply to each of the microorganisms of that strain. Similarly, the characteristics described for any one of the microorganisms of the strain apply to the entire set of the microorganisms of that strain.

The microorganisms optimized according to the invention include bacteria, yeasts and filamentous moulds, and in particular bacteria and yeasts belonging to the following species: *Aspergillus* sp., *Bacillus* sp., *Brevibacterium* sp., *Clostridium* sp., *Corynebacterium* sp., *Escherichia* sp., *Gluconobacter* sp., *Penicillium* sp., *Pichia* sp., *Pseudomonas* sp., *Rhodococcus* sp., *Saccharomyces* sp., *Streptomyces* sp., *Xanthomonas* sp., *Candida* sp.

The principle of optimization of the NADPH/NADP$^+$ ratio is described below for *E. coli* and *S. cerevisiae*. The same principle can be similarly applied to all microorganisms grown in aerobic conditions.

The principle of optimisation of the NADPH/NADP$^+$ ratio consists in limiting the enzyme activities involved in the oxidation of NADPH, and/or favouring the enzyme activities that allow the reduction of NADP$^+$. The enzyme activities involved in the oxidation of NADPH are limited by reducing, and in particular by inactivating, those activities, especially activities such as quinone oxidoreductase and/or soluble transhydrogenase. The enzyme activities that favour the reduction of NADP$^+$ are enhanced by setting the carbon flux via the pentose phosphate cycle and/or by modifying the cofactor specificity of at least one enzyme so that it uses NADP in preference to NAD, its usual cofactor.

The strains optimized according to the invention are obtained by molecular biology methods. Those skilled in the art know the protocols used to modify the genetic character of microorganisms. These methods are documented and can be readily implemented by those skilled in the art (Sambrook et al., 1989 Molecular cloning: a laboratory manual. 2$^{nd}$ Ed. Cold Spring Harbor Lab., Cold Spring Harbor, N.Y.).

The methods used to limit an enzyme activity consist in modifying the gene that expresses it by means of an appropriate method, for example by causing one or more mutations in the coding part of the gene concerned, or by modifying the promoter region, in particular by replacing it with a sequence that reduces the gene expression.

The methods used to inactivate an enzyme consist in inactivating the product of the expression of the gene concerned by means of an appropriate method, or in inhibiting the expression of the gene concerned, or in deleting at least a part of the gene concerned so that its expression is prevented (for example deleting part or all of the promoter region necessary for its expression), or so that the expression product loses its function (for example by deletion in the coding part of the gene concerned).

Preferentially, the deletion of a gene comprises the removal of that gene, and if required its replacement by a selection marker gene to facilitate the identification, isolation and purification of the strains optimized according to the invention.

The inactivation of a gene in *E. coli* is preferably carried out by homologous recombination (Datsenko K. A., Wanner B. L. (2000) One-step inactivation of chromosomal genes in *Escherichia coli* K-12 using PCR products. *Proc. Natl. Acad. Sci. USA* 97: 6640-6645). The principle of a protocol is briefly as follows: a linear fragment, obtained in vitro, comprising the two regions flanking the gene, and at least one selection gene located between these two regions (generally an antibiotic resistance gene), is introduced into the cell. This fragment thus contains an inactivated gene. Cells that have undergone a recombination event and integrated the introduced fragment are then selected by plating on a selective medium. Cells that have undergone a double recombination event, in which the wild gene has been replaced by the inactivated gene, are then selected. This protocol can be improved by using positive and negative selection systems, in order to speed up the detection of double recombination events.

The inactivation of a gene in *S. cerevisiae* is also performed preferentially by homologous recombination (Baudin et al., *Nucl. Acids Res.* 21, 3329-3330, 1993; Wach et al., *Yeast* 10, 1793-1808, 1994; Brachmann et al., *Yeast.* 14:115-32, 1998).

The processes that favour an enzyme activity involve stabilizing the product of the expression of the gene concerned by appropriate means, for example by diminishing its sensitivity to allosteric effectors, or by enhancing the expression of the gene so as to increase the quantity of enzyme produced.

The overexpression of a gene can be achieved by replacing the promoter of the gene in situ by a strong or inducible promoter. Alternatively, a replicative plasmid (single or multiple copy) is introduced into the cell in which the gene to be overexpressed is under the control of the appropriate promoter. In the case of modification of *Escherichia coli*, it is possible, for example, to use the promoters Plac-o, Ptrc-o, and ptac-o, three strong bacterial promoters for which the lac operator (lacO) has been deleted to make them constitutive. In the case of modifications of *Saccharomyces cerevisiae*, it is possible, for example, to use the promoters Ppgk, Padh1, Pgal1, Pgal10.

The processes that can be used to modify the cofactor specificity of an enzyme so that it uses NADP in preference to NAD involve modifying the sequence of the gene that allows the expression of that enzyme (Bocanegra, J. A. Scrutton, N. S.; Perham, R. N. (1993) Creation of an NADP-dependent pyruvate dehydrogenase multienzyme complex by protein engineering. *Biochemistry* 32: 2737-2740).

The strains optimized according to the invention, i.e. with enhanced capacity for $NADP^+$ reduction, are characterized by the attenuation or inactivation of one or more NADPH-oxidizing enzyme activities, and in particular activities of the quinone oxidoreductase and/or soluble transhydrogenase type.

Below are listed some non-limiting examples of activities and genes of NADPH-oxidizing enzymes:

| Enzyme activity | EC number | *E. coli* gene | *S. cerevisiae* gene |
|---|---|---|---|
| Alcohol dehydrogenase | 1.1.1.2 | yahK | ADH6 |
| Aldose reductase | 1.1.1.21 | | GRE3 |
| Shikimate dehydrogenase | 1.1.1.25 | aroE | ARO1 |
| Methylglyoxal reductase | 1.1.1.78 | | GRE2p |
| Gamma-glutamyl phosphate reductase | 1.2.1.41 | proA | PRO2 |
| 2,4-dienoyl coenzyme A reductase | 1.3.1.34 | fadH | |
| Glutamate dehydrogenase | 1.4.1.4 | gdhA | GDH1, GDH2 |
| Glutamate synthase | 1.4.1.13 | gltB, gltD | GLT1 |
| Methylenetetrahydrofolate dehydrogenase | 1.5.1.5 | folD | ADE3, MIS1 |
| Soluble transhydrogenase | 1.6.1.1 | udhA | |
| Membrane-bound transhydrogenase | 1.6.1.2 | pntA, pntB | |
| Quinone oxidoreductase | 1.6.5.5 | qor | ZTA1 |
| Nitrite reductase | 1.7.1.4 | nirB, nirD | |
| Sulphite reductase | 1.8.1.2 | cysI, cysJ | |

| Enzyme activity | EC number | *E. coli* gene | *S. cerevisiae* gene |
|---|---|---|---|
| Sterol demethylase | 1.14.13.70 | | ERG11 |
| 4-Hydroxy-3-methylbut-2-enyl diphosphate reductase | 1.17.1.2 | ispH | |
| Flavodoxin reductase | 1.18.1.2 | fpr | |

The strains optimized according to the invention (i.e. with enhanced capacity for $NADP^+$ reduction) also include modifications that favour one or more $NADP^+$-reducing enzyme activities, and in particular modifications that set the carbon flux via the pentose phosphate pathway, and/or modifications concerning the cofactor specificity of at least one enzyme, so that it utilizes NADP in preference to NAD, its usual cofactor.

The activities that are susceptible to modification in the optimized strains according to the invention (i.e. with enhanced capacity for $NADP^+$ reduction) to favour one or more $NADP^+$-reducing enzyme activities are listed below:

| Enzyme activity | EC number | *E. coli* gene | *S. cerevisiae* gene |
|---|---|---|---|
| Phosphoglucose isomerase | 5.3.1.9 | pgi | PGI2 |
| Phosphofructokinase | 2.7.1.11 | pfkA, pfkB | PFK1, PFK2 |
| Glucose 6-phosphate dehydrogenase | 1.1.1.49 | zwf | ZWF1 |
| 6-Phosphogluconolactonase | 3.1.1.31 | | SOL1, SOL2, SOL3, SOL4 |
| 6-Phosphogluconate dehydrogenase | 1.1.1.44 | gnd | GND1, GND2 |
| 6-Phosphogluconate dehydratase | 4.2.1.12 | edd | |
| Malate synthase | 2.3.3.9 | aceB | DAL7 |
| Isocitrate lyase | 4.1.3.1 | aceA | ICL1 |
| Isocitrate dehydrogenase | 1.1.1.42 | icd | IDP1, IDP2, IDP3 |
| Isocitrate dehydrogenase kinase/phosphatase | 2.7.1.116 | aceK | |
| Dihydrolipoamide dehydrogenase | 1.8.1.4 | lpd | LPD1 |
| Glyceraldehyde-3-phosphate dehydrogenase | 1.2.1.12 | gapA, gapC | TDH1, TDH2, TDH3 |

The enzyme activities susceptible to modification in the optimized strains according to the invention are mainly defined using the denomination of the protein or gene in *E. coli* or *S. cerevisiae*. However, this usage has a more general meaning according to the invention, and covers the corresponding enzyme activities in other microorganisms. Using the sequences of proteins and genes in *E. coli* or *S. cerevisiae*, those skilled in the art can identify the equivalent genes in microorganisms other than *E. coli* or *S. cerevisiae*.

The means of identifying homologous sequences and their percentages of homology are well known to those skilled in the art, and include, in particular, the BLAST program, which can be used from the website www.ncbi.nlm.nih.gov/BLAST with the default parameters indicated there. The sequences obtained can then be exploited (e.g. aligned) using, for example, the CLUSTALW program (www.ebi.ac.uk/clustalw) or the MULTALIN program (www.orodes.toulouse.inra.fr/multalin/cgi-bin/multalin.pl), with the default parameters indicated on their websites Alternatively, the CD-Search program (www.ncbi.nih.gov/Structure/cdd/wrpsb.cgi) can be used to identify the conserved domains in the protein sequences of *E. coli* or *S. cerevisiae*, and to seek the sequences of other microorganisms presenting the same domain or domains. The conserved domains are recorded in the CDD database (Conserved domain database; Marchler-Bauer A, Anderson J B, DeWeese-Scott C, Fedorova N D, Geer L Y, He S, Hurwitz D I, Jackson J D, Jacobs A R, Lanczycki C J, Liebert C A, Liu C, Madej T, Marchler G H, Mazumder R, Nikolskaya A N, Panchenko A R, Rao B S, Shoemaker B A, Simonyan V, Song J S, Thiessen P A, Vasudevan S, Wang Y, Yamashita R A, Yin J J, Bryant S H. CDD: a curated Entrez database of conserved domain alignments. *Nucleic Acids Research* 31:383-387 (2003)) which groups data of the PFAM or COG type.

The PFAMs (Protein FAMilies database of alignments and hidden Markov models; www.sanger.ac.uk/Software/Pfam) are a large collection of alignments of protein sequences. Each PFAM makes it possible to visualize multiple alignments, see protein domains, evaluate distribution among organisms, access other databases, and visualize known protein structures.

The COGs (Clusters of Orthologous Groups of proteins; www.ncbi.nlm.nih.gov/COG/) are obtained by comparing protein sequences from 43 fully sequenced genomes representing 30 major phylogenetic lines. Each COG is defined from at least three lines, thus making it possible to identify ancient conserved domains.

From consensus sequences identified by these different methods, it is possible to design degenerate oligonucleotide probes to clone the corresponding gene in another microorganism. These routine molecular biology methods are well known to those skilled in the art and are described, for example, in Sambrook et al. (1989 Molecular cloning: a laboratory manual. $2^{nd}$ Ed. Cold Spring Harbor Lab., Cold Spring Harbor, N.Y.).

Examples of Genes Coding for Proteins Analogous to the Soluble Transhydrogenase of *E. coli* Coded for by the udhA Gene:

| Gene | Microorganism |
| --- | --- |
| sth | *Azotobacter vinelandii* |
| udhA | *Salmonella typhimurium* LT2 |
| sthA | *Pseudomonas aeruginosa* PA01 |
| sth | *Pseudomonas fluorescens* |
| sthA | *Pseudomonas putida* KT2440 |
| udhA | *Shigella flexneri* 2a str. 301 |
| sthA | *Vibrio cholera* |
| sthA | *Yersinia pestis* |

Examples of Genes Coding for Proteins Analogous to the Quinone Oxidoreductase of *E. coli* Coded for by the qor gene:

| Gene | Microorganism |
| --- | --- |
| qor | *Bradyrhizobium japonicum* USDA 110 |
| qor | *Brucella suis* 1330 |
| CC3759 | *Caulobacter crescentus* |
| mll0505 | *Mesorhizobium loti* |
| qor | *Mycobacterium tuberculosis* H37RV |
| qor | *Pseudomonas aeruginosa* |
| ZTA1 | *S. cerevisiae* |
| SPCC285.01c | *Schizosaccharomyces pombe* |
| drgA | *Synechocystis* sp. PCC6803 |
| qorA | *Staphylococcus aureus* |
| TTC0305 | *Thermus thermophilus* HB8 |
| qor | *Yersinia pestis* CO92 |

The strains optimised according to the invention (i.e. with enhanced capacity for NADP$^+$ reduction) are characterized by the deletion of at least one gene coding for a NADPH-oxidizing activity, and in particular, the deletion of a gene coding for a quinone oxidoreductase (e.g. qor, ZTA1) and/or a gene coding for a soluble transhydrogenase activity (e.g. udhA).

In a preferred embodiment of the invention the udhA and qor genes are both deleted.

In a specific embodiment of the invention the strains optimized according to the invention are also characterized by the deletion of one or several genes coding for phosphoglucose isomerase activity (e.g. pgi, PGI1) and/or phosphofructokinase activity (e.g. pfkA, PFK1).

In a further specific embodiment of the invention the strains optimized according to the invention are also characterized by the modification of one or several genes coding for dihydrolipoamide dehydrogenase (e.g. lpd, LPD1) and/or glyceraldehyde 3-phosphate dehydrogenase (e.g. gapA, TDH1) activities, which modification consists in causing the enzyme to prefer NADP over NAD, its usual cofactor.

The strains of the invention characterized by the deletion of genes coding for phosphoglucose isomerase and/or phosphofructokinase activities are particularly well suited to biotransformation processes.

To increase the quantity of NADPH available in the microorganisms optimized according to the invention, it can be advantageous to overexpress at least one gene coding for one of the following enzyme activities: glucose 6-phosphate dehydrogenase (e.g. zwf, ZWF1), 6-phosphogluconolactonase (e.g. SOL1), 6-phosphogluconate dehydrogenase (e.g. gnd, GND1), isocitrate dehydrogenase (e.g. icd, IDP1) and membrane-bound transhydrogenase (e.g. pntA), and/or to delete at least one gene coding for one of the following enzyme activities: phosphogluconate dehydratase (e.g. edd), malate synthase (e.g. aceB, DAL7), isocitrate lyase (e.g. aceA, ICL1) and isocitrate dehydrogenase kinase/phosphatase (e.g. aceK).

A further object of the present invention is a microorganism optimized for the production of NADPH as defined above and below, which microorganism also contains one or several genes coding for enzyme activities involved in the biotransformation of a substance of interest, and one or several selection marker genes.

These genes can be native to the strain optimized by the invention, or be introduced into the strain optimized by the invention by conversion using a suitable vector, either by integration in the genome of the microorganism or by a replicative vector, which suitable vector bears one or several genes coding for the relevant enzymes involved in the biotransformation of the relevant substance of interest and/or the relevant selection markers.

These genes include a nucleic acid sequence coding for an enzyme involved in the biotransformation of the substance of interest and/or for a selection marker, which coding sequence is merged with efficient promoter sequences in the prokaryote and/or eukaryote cell selected for biotransformation. The vector (or plasmid) can be a shuttle vector between *E. coli* and another microorganism.

The choice of the strain optimized for the NADPH/NADP$^+$ ratio will be determined according to the type of biotransformation (fermentation or bioconversion), the total demand for NADPH in the bioconversion pathway considered, the nature of the carbon source or sources, the biomass flux demand, etc.

The deletion of genes coding for phosphoglucose isomerase and/or phosphofructokinase activities will be necessary if it is not possible to control the distribution of the carbon flux between glycolysis and the pentose phosphate pathway. The deletion of genes coding for phosphoglucose isomerase will be preferred for fermentations or when the demand for NADPH requires a minimum reduction flux of 2 moles of $NADP^+$ per mole of imported glucose. The deletion of genes coding for phosphofructokinase will be chosen preferentially for bioconversions or when the demand for NADPH requires a minimum reduction flux of 3-4 moles of $NADP^+$ per mole of imported glucose. The modification, as described above and below, of genes coding for dihydrolipoamide dehydrogenase and/or glyceraldehyde 3-phosphate dehydrogenase will be carried out when biotransformations require a minimum reduction flow greater than 3 moles of $NADP^+$ per mole of imported glucose and in particular to optimize the strains E. coli Δ(udhA, qor) or E. coli Δ(udhA, qor, pgi) or E. coli Δ(udhA, qor, pfkA, pfkB). The other stated modifications, namely the overexpression of at least one gene coding for one of the following enzyme activities: glucose 6-phosphate dehydrogenase, 6-phosphogluconolactonase, 6-phosphogluconate dehydrogenase, isocitrate dehydrogenase and membrane transhydrogenase, and/or deletion of at least one gene coding for one of the following enzyme activities: 6-phosphogluconate dehydratase, malate synthase, isocitrate lyase or isocitrate dehydrogenase kinase/phosphatase, can be carried out to fine-tune the optimization of the $NADPH/NADP^+$ ratio to the needs of the cell and of the biotransformation process being considered.

The present invention also concerns a procedure for preparing strains optimized according to the invention as defined above and below, characterized by the deletion of a gene coding for quinone oxidoreductase or soluble transhydrogenase activities, and possibly by the deletion of a gene coding for glucose 6-phosphate dehydrogenase or 6-phosphogluconolactonase activities, and/or by the modification of at least one gene coding for NAD enzymes, in particular for dihydrolipoamide dehydrogenase or glyceraldehyde 3-phosphate dehydrogenase, so that they preferentially use NADP, and if required, by the deletion of at least one gene coding for 6-phosphogluconate dehydratase, malate synthase, isocitrate lyase or isocitrate dehydrogenase kinase/phosphatase, which deletions and modifications are carried out by suitable means, and/or characterized by the overexpression of at least one gene coding for the following activities: glucose 6-phosphate dehydrogenase, 6-phosphogluconolactonase, 6-phosphogluconate dehydrogenase, isocitrate dehydrogenase or membrane transhydrogenase, either by modifying the strain using a suitable vector that allows the overexpression, or by modifying the strength of the endogenous promoter controlling the gene that is to be overexpressed.

In a specific embodiment of the invention, the process for preparing strains according to the invention also includes the conversion of the optimized strains with at least one suitable vector that includes one or more genes coding for one or more enzymes involved in the biotransformation of a substance of interest, and one or more selection marker genes.

A further object of the invention concerns the use of these strains optimized according to the invention for NADPH-dependent biotransformations, thereby obtaining an improved biotransformation yield compared with a strain not optimized for NADPH.

The biotransformations will be carried out using strains defined according to the invention in which genes will be expressed that code for enzyme activities catalyzing NADPH-dependent reactions. Those skilled in the art can easily identify such enzymes. They include the following among others: EC 1.1.1.10 L-xylulose reductase, EC 1.1.1.21 methylglyoxal reductase, EC 1.1.1.51 3(or 17)β-hydroxysteroid dehydrogenase, EC 1.1.1.54 allyl-alcohol dehydrogenase, EC 1.1.1.80 isopropanol dehydrogenase, EC 1.1.1.134 dTDP-6-deoxy-L-talose 4-dehydrogenase, EC 1.1.1.149 20α-hydroxysteroid dehydrogenase, EC 1.1.1.151 21-hydroxysteroid dehydrogenase, EC 1.1.1.189 prostaglandin-$E_2$ 9-reductase, EC 1.1.1.191 indole-3-acetaldehyde reductase EC 1.1.1.207 (−)-menthol dehydrogenase, EC 1.1.1.234 flavanone 4-reductase, EC 1.2.1.50 long-chain-fatty-acyl-CoA reductase, EC 1.3.1.4 cortisone α-reductase, EC 1.3.1.23 cholestenone 5β-reductase, EC 1.3.1.70 $\Delta^{14}$-sterol reductase, EC 1.4.1.12 2,4-diaminopentanoate dehydrogenase, EC 1.5.1.10 saccharopine dehydrogenase, L-glutamate-forming, EC 1.7.1.6 azobenzene reductase, EC 1.8.1.5 2-oxopropyl-CoM reductase (carboxylating), EC 1.10.1.1 trans-acenaphthene-1,2-diol dehydrogenase, EC 1.14.13.7 phenol 2-monooxygenase, EC 1.14.13.12 benzoate 4-mono-oxygenase, EC 1.14.13.26 phosphatidylcholine 12-mono-oxygenase, EC 1.14.13.64 4-hydroxybenzoate 1-hydroxylase, EC 1.14.13.70 sterol 14-demethylase, EC 1.16.1.5 aquacobalamine reductase, EC 1.17.1.1 CDP-4-dehydro-6-deoxyglucose reductase, EC 1.18.1.2 ferredoxin-NADP reductase.

The invention also concerns a process for producing a substance of interest formed by a biosynthesis route that includes at least one NADPH-dependent reaction, characterized in that it comprises the following steps:

a) Growth in culture of microorganisms optimized according to the invention in an appropriate culture medium that favours their growth and that contains the substances necessary to carry out the biotransformation by fermentation or bioconversion, except NADPH.

b) Extraction of the substance of interest from the medium and its purification if necessary.

Preferably, the substance of interest can be an amino acid, a vitamin, a sterol, a flavonoid, a fatty acid, an organic acid, a polyol, or a hydroxyester. Amino acids and their precursors include in particular lysine, methionine, threonine, proline, glutamic acid, homoserine, isoleucine, and valine. Vitamins and their precursors include in particular pantoate, trans-neurosporene, phylloquinone and tocopherols. Sterols include in particular squalene, cholesterol, testosterone, progesterone and cortisone. Flavonoids include in particular frambinone and vestitone. Organic acids include coumaric acid and 3-hydroxypropionic acid. Polyols include sorbitol, xylitol and glycerol. Hydroxyesters include ethyl-3-hydroxybutyrate and ethyl-4-chloro-3-hydroxybutyrate.

In the case of a bioconversion, the process also includes the addition to the appropriate culture medium of the substrate that is to be converted.

The culture medium mentioned in step b) of the process according to the invention described above contains at least one assimilable carbohydrate that can be any of various assimilable sugars, such as glucose, galactose, sucrose, lactose, molasses, or by-products of these sugars. A simple source of carbon that is especially preferred is glucose. Another preferred simple carbon source is sucrose. The culture medium can also contain one or more substances (e.g. amino acids, vitamins or mineral salts) that favour the growth of the microorganism and/or the production of the substance of interest. In particular, the mineral culture medium for E. coli can thus have a composition identical or similar to an M9 medium (Anderson, 1946, Proc. Natl. Acad. Sci. USA 32:120-128), an M63 medium (Miller, 1992; A Short Course in Bacterial Genetics: A Laboratory Manual and Handbook for Escherichia coli and Related Bacteria, Cold Spring Harbor Laboratory Press, Cold Spring Harbor, N.Y.) or a medium such as that described by Schaefer et al. (1999, Anal. Biochem. 270: 88-96).

The biotransformation conditions are set by those skilled in the art. In particular, the microorganisms are fermented at a temperature between 20° C. and 55° C., preferably between 25° C. and 40° C., and preferably at about 30° C. for *S. cerevisiae* and at about 37° C. for *E. coli*.

The following examples are given for illustration only and in no way restrict the embodiments or the scope of the invention.

EXAMPLE 1

Calculation of Theoretical Optimal Yields for the Bioconversion of Ethylacetoacetate into ethyl-3-hydroxybutyrate a) Bioconversion with *E. coli*

Predictive modelling was carried out using the algorithm MetOpt®-Coli, a stoichiometric model developed by the company METabolic EXplorer, with which it was possible to determine 1) the maximum production yield of ethyl-3-hydroxybutyrate from ethylacetoacetate, and 2) the best flux distribution from glucose to meet the needs for growth and redox equilibria that are necessary for the cell to grow and reach the maximum bioconversion yield.

Specific settings of model variables were 1) a glucose import flux of 3 mmol·g$^{-1}$·h$^{-1}$, 2) a variable growth rate of 0, 0.15 and 0.25 h$^{-1}$, 3) a variable membrane-bound transhydrogenase flux (pntAB) less than or equal to 1 mmol·g$^{-1}$·h$^{-1}$; the limiting value of the membrane-bound transhydrogenase flux was determined from the literature (Hanson, 1979; Anderlund et al., 1999; Emmerling et al., 2002), and 4) a maintenance flux limited at between 5 and 22 mmol·g$^{-1}$·h$^{-1}$.

In all cases the model suggested the deletion of the udhA and qor genes. In practice, however, the strain *E. coli* [Δ(udhA, qor)] does not afford a yield equivalent to the theoretical optimal yield, as it is difficult to maintain a suitable distribution of carbon flux between the pentose phosphate pathway and glycolysis, this distribution being variable according to the growth rate. In practice therefore, the strains *E. coli* [Δ(udhA, qor, pfkA, pfkB)] or [Δ(udhA, qor, pgi)] are preferred, the choice between them depending on the growth rate of the strain during the bioconversion process.

The theoretical optimal yields for the bioconversion of ethylacetoacetate into ethyl-3-hydroxybutyrate were calculated for different strains of *E. coli* optimized according to the invention.

Theoretical Optimal Yields for the Bioconversion of Ethylacetoacetate into ethyl-3-hydroxybutyrate (Mol Per Mol of Glucose) by Strains of *E. coli* Optimized for NADP$^+$ Reduction Capacity To further improve the theoretical optimal yield of the strains optimized according to the invention, additional modifications can be made, such as the overexpression of at least one gene that can be zwf, gnd, pntA, pntB or icd and/or the deletion of at least one gene that can be edd, aceA, aceB or aceK.

b) Bioconversion with *S. cerevisiae*

Predictive modelling was carried out using the algorithm MetOpt®-Scere, a stoichiometric model developed by the Company, with which it was possible to determine 1) the maximum production yield of ethyl-3-hydroxybutyrate from ethylacetoacetate, 2) the best flux distribution from glucose to meet the needs of the growth and redox equilibria necessary for the cell to grow and reach the maximum bioconversion yield.

Specific settings of model variables were 1) a glucose import flux of 3 mmol·g$^{-1}$·h$^{-1}$, 2) a variable growth rate of 0, 0.15 and 0.25 h$^{-1}$, 3) a maintenance flux de maintenance less than or equal to 22 mmol·g$^{-1}$·h$^{-1}$, 4) aldehyde dehydrogenase reactions (ALD2, ALD3, ALD6) irreversible and set in the direction acetate+NAD(P)H→acetaldehyde+NAD(P), and 5) no activities equivalent to udhA or pntA,B.

The model allowed for mitochondrial and peroxisomal compartmentalization.

In all cases, the model suggested the deletion of a gene coding for an enzyme oxidizing NADPH, and in particular gene ZTA1. However, in practice, the strain *S. cerevisiae* [ΔZTA1] does not provide a yield equivalent to the theoretical optimum yield, as it is difficult to maintain a suitable distribution of carbon flux between the pentose phosphate and glycolysis pathways, because this distribution varies with the growth rate. In practice it is preferable to use the strains *S. cerevisiae* [Δ(ZTA1, PFK1, PFK2)] or [Δ(ZTA1, PGI1)], the choice between them depending on rate of growth of the strain during the bioconversion process.

The theoretical optimal yields for the bioconversion of ethylacetoacetate into ethyl-3-hydroxybutyrate were calculated for different strains of *S. cerevisiae* optimized according to the invention.

| | $\mu = 0$ | $\mu = 0.15$ h$^{-1}$ | $\mu = 0.25$ h$^{-1}$ |
|---|---|---|---|
| Δ(udhA, qor, pgi) | 1.82 | 1.74 | 1.22 |
| Δ(udhA, qor, pgi) gapA-NADP-dependent | 4.29 | 3.64 | 2.43 |
| Δ(udhA, qor, pgi) lpd-NADP-dependent | 5.67 | 3.46 | 1.99 |
| Δ(udhA, qor, pgi) gapA-NADP-dependent lpd-NADP-dependent | 6.86 | 4.96 | 3.33 |
| Δ(udhA, qor, pfkA, pfkB) | 6.76 | 4.65 | 0.19 |
| Δ(udhA, qor, pfkA, pfkB) gapA-NADP-dependent | 8.16 | 5.54 | 1.02 |
| Δ(udhA, qor, pfkA, pfkB) lpd-NADP-dependent | 8.33 | 5.60 | 1.77 |
| Δ(udhA, qor, pfkA, pfkB) gapA-NADP-dependent lpd-NADP-dependent | 9.33 | 6.38 | 2.60 |

| | $\mu = 0$ | $\mu = 0.15$ h$^{-1}$ | $\mu = 0.25$ h$^{-1}$ |
|---|---|---|---|
| Δ(ZTA1, PGI1) | 2.42 | 2.00 | 1.73 |
| Δ(ZTA1, PGI1) TDH1,2,3-NADP-dependent | 4.22 | 3.50 | 3.03 |
| Δ(ZTA1, PGI1) LPD1-NADP-dependent | 4.08 | 3.29 | 2.77 |
| Δ(ZTA1, PGI1) TDH1,2,3-NADP-dependent LPD1-NADP-dependent | 6.17 | 5.01 | 4.23 |
| Δ(ZTA1, PFK1, PFK2) | 12.00 | 8.18 | 5.64 |
| Δ(ZTA1, PFK1, PFK2) TDH1,2,3-NADP-dependent | 12.00 | 9.11 | 7.19 |
| Δ(ZTA1, PFK1, PFK2) LPD1-NADP-dependent | 12.00 | 8.44 | 6.06 |
| Δ(ZTA1, PFK1, PFK2) TDH1,2,3-NADP-dependent LPD1-NADP-dependent | 12.00 | 9.28 | 7.46 |

Theoretical Optimal Yields for the Bioconversion of Ethylacetoacetate into ethyl-3-hydroxybutyrate (Mol Per Mol of Glucose) by Strains of *S. cerevisiae* Optimized for NADP$^+$ Reduction Capacity To further improve the theoretical optimum yield of the strains optimized according to the invention, additional modifications can be made, such as the overexpression of at least one gene that can be ZWF, SOL1, SOL2, SOL3, SOL4, GND1, GND2, IDP1, IDP2 or IDP3 and/or the deletion of at least one gene that can be either ICL1 or DAL7.

EXAMPLE 2

Construction of the Strain *E. coli* [Δ(udhA, qor)]

The inactivation of the udhA gene was achieved by homologous recombination using the method described by Datsenko and Wanner (One-step inactivation of chromosomal genes in *Escherichia coli* K-12 using PCR products, *Proc. Natl. Acad. Sci. USA*, 2000, 97: 6640-6645).

This method consists in inserting an antibiotic (chloramphenicol) resistance cassette while at the same time deleting most of the gene concerned. For this purpose a pair of oligonucleotides was synthesized, each consisting of 100 pb of which 80 pb (lower case) were homologous with the gene to be deleted (e.g. udhA) and 20 pb (upper case) were homologous with the chloramphenicol resistance cassette.

```
DudhAF
ggtgcgcgcgtcgcagttatcgagcgttatcaaaatgttggcggcggttg
cacccactggggcaccatcccgtcgaaagcCATATGAATATCCTCCTTAG DudhAR
Cccagaatctcttttgtttcccgatggaacaaaattttcagcgtgcccac
gttcatgccgacgatttgtgcgcgtgccagTGTAGGCTGGAGCTGCTTCG
```

The antibiotic cassette carried by the plasmid pKD3 was amplified by PCR using the oligonucleotides DudhAF and DudhAR. The PCR product obtained was then introduced by electroporation into the strain *E. coli* [pKD46], which carries the gene coding for Red recombinase, an enzyme that catalyzes homologous recombination. The chloramphenicol-resistant transformants were then selected and the insertion of the resistance cassette was checked by PCR analysis using the oligonucleotides UdhAF and UdhAR:

```
UdhaF
Ggccgctcaggatatagccagataaatgac

UdhaR
Gcgggatcactttactgccagcgctggctg
```

The chloramphenicol resistance cassette was then removed. To do this, the plasmid pCP20 carrying the FLP recombinase acting on the FRT sites of the chloramphenicol resistance cassette was introduced into the recombinant strains by electroporation. After a series of cultures at 42° C., the loss of the antibiotic resistance cassette was checked by PCR analysis with the oligonucleotides UdhAF and UdhAR.

The inactivation of the gene qor was carried out by the same method using the following oligonucleotides:

```
DqorF
ggtggcccggaagtacttcaagccgtagagttcactcctgccgatccggc
ggagaatgaaatccaggtcgaaaataaagcCATATGAATATCCTCCTTAG DqorR
cgcccggctttccagaatctcatgcgcacgctgcgcatccttcagcggat
atttctgctgctcggcgacatcgaccttaaTGTAGGCTGGAGCTGCTTCG QorF
Cgcccaacaccgactgctccgcttcgatcg QorR
cagcgttatgaccgctggcgttactaaggg
```

For practical reasons it can be useful to delete the two genes simultaneously. To do this each gene was replaced by a different antibiotic resistance cassette (e.g. chloramphenicol for udhA and kanamycin for qor).

The strain obtained was thus *E. coli* [Δ(udhA, qor)].

EXAMPLE 3

Construction of the Plasmid pSK-PgapA-GRE2p, Introduction into the Strain *E. coli* [Δ(udhA, qor)] and Bioconversion of Ethylacetoacetate into ethyl-3-hydroxybutyrate The plasmid pSK-PgapA was constructed by insertion of the promoter gapA in the vector pBluescript-SK (pSK). To do this, the promoter gapA of *E. coli* was amplified with polymerase Pwo from chromosomal DNA.

The PCR product obtained was then digested by the restriction enzyme HindIII and ligated to the vector pSK digested by the restriction enzyme HindIII and dephosphorylated to give the plasmid pSK-PgapA. The vector pSK carried a replication origin for *E. coli* and an ampicillin resistance gene.

The plasmid pSK-PgapA was then introduced into the strain *E. coli* DH5α for verification of the construction. The sequencing of the promoter gapA of the plasmid pSK-PgapA with the oligonucleotide universal M13 forward was then carried out to confirm the construction.

The plasmid pSK-PgapA-GRE2p was constructed by insertion of the gene GRE2p in the plasmid pSK-PgapA. To do this, the gene GRE2p of *Saccharomyces cerevisiae* was amplified with polymerase Pwo from chromosomal DNA using the following oligonucleotides:

```
Ome119_GRE2F (NdeI)
Acgtacgtggcatatgcagttttcgtttcaggtgctaacggg

Ome120_GRE2R (PstI)
Acgtacctgcagttatattctgccctcaaattttaaaatttggg
```

The PCR product obtained was then digested by restriction enzymes NdeI-PstI and ligated to the vector pSK-PgapA digested by the restriction enzymes NdeI-PstI and dephosphorylated to give the plasmid pSK-PgapA-GRE2p. The plasmid pSK-PgapA carried a replication origin for *E. coli* and an ampicillin resistance gene.

The plasmid pSK-PgapA-GRE2p was then introduced into the strain *E. coli* DH5α to check the construction. The sequencing of the gene GRE2p of the plasmid pSK-PgapA-GRE2p with the oligonucleotide universal M13 reverse and universal M13 forward was then carried out to confirm the construction.

The validated plasmid was introduced into the strain *E. coli* [Δ(udhA, qor)] (Example 2) by electroporation.

The strain obtained, *E. coli* [Δ(udhA, qor) pSK-PgapA-GRE2p], was then grown in minimum medium containing glucose and ethylacetoacetate. A strain of *E. coli* [pSK-PgapA-GRE2p] was grown in the same conditions.

When growth was completed the following variables were compared:
  The time course of the biomass of each strain during the bioconversion phase.
  The quantity of ethyl-3-hydroxybutyrate produced in the extracellular medium.
  The quantity of ethyl-3-hydroxybutyrate accumulated in the cells.
  The productivity in terms of ethyl-3-hydroxybutyrate.
  The yield glucose/ethyl-3-hydroxybutyrate.

It was found that the strain E. coli [Δ(udhA, qor) pSK-PgapA-GRE2p] gave a greater production yield of ethyl-3-hydroxybutyrate than the non-optimized strain.

EXAMPLE 4

Construction of the Strain E. coli [Δ(udhA, qor, pgi) pSK-PgapA-GRE2p] and Bioconversion of Ethylacetoacetate into ethyl-3-hydroxybutyrate The inactivation of the gene pgi was carried out in the strain E. coli [Δ(udhA, qor)] (Example 2) using the method described in Example 2, and the following oligonucleotides:

```
DpgiF
ccaacgcagaccgctgcctggcaggcactacagaaacacttcgatgaaat
gaaagacgttacgatcgccgatcttttgcTGTAGGCTGGAGCTGCTTCG DpgiR
gcgccacgctttatagcggttaatcagaccattggtcgagctatcgtggc
tgctgatttctttatcatctttcagctctgCATATGAATATCCTCCTTAG pgiF
gcggggcggttgtcaacgatggggtcatgc pgiR
cggtatgatttccgttaaattacagacaag
```

The construction was carried out in rich medium (e.g. LB). The plasmid pSK-PgapA-GRE2p was then introduced into the strain obtained (Example 3) by electroporation, and the resulting strain E. coli [Δ(udhA, qor, pgi) pSK-PgapA-GRE2p] was selected on rich medium.

The strain obtained was then grown on minimum medium containing glucose and ethylacetoacetate. A strain of E. coli [pSK-PgapA-GRE2p] was grown under the same conditions.

When growth was completed the following variables were compared:
  The time course of the biomass of each strain during the bioconversion phase.
  The quantity of ethyl-3-hydroxybutyrate produced in the extracellular medium.
  The quantity of ethyl-3-hydroxybutyrate accumulated in the cells.
  The productivity in terms of ethyl-3-hydroxybutyrate.
  The yield glucose/ethyl-3-hydroxybutyrate.

We observed that the strain E. coli [Δ(udhA, qor, pgi) pSK-PgapA-GRE2p] gave a greater production yield of ethyl-3-hydroxybutyrate than the non-optimized strain.

|  | $mol_{EHB}/mol_{Glucose}$ |
|---|---|
| MG1655 pSK-PgapA-GRE2p | 0.75 |
| MG1655 Δ(udhA, qor, pgi) pSK-PgapA-GRE2p | 2.12 |

EXAMPLE 5

Construction of the Strain E. coli [Δ(udhA, qor, pgi, edd) pSK-PgapA-GRE2p] and Bioconversion of Ethylacetoacetate into ethyl-3-hydroxybutyrate The inactivation of the gene edd was carried out in the strain E. coli [Δ(udhA, qor, pgi)] (Example 4) using the method described in Example 2, and the following oligonucleotides:

```
DeddF (1932582-1932499)
Cgcgcgagactcgctctgcttatctcgcccggatagaacaagcgaaaact
tcgaccgttcatcgttcgcagttggcatgcggTGTAGGCTGGAGCTGCTT
CG DeddR (1930866-1930943)
cgcaaggcgctgaataattcacgtcctgttcccacgcgtgacgcgctcag
gtcaggaatgtgcggttcgcgagcagccCATATGAATATCCTCCTTAG EddF (1932996-1932968)
Gggtagactccattactgaggcgtgggcg EddR (1930439-1930462)
Ccccggaatcagaggaatagtccc
```

The construction was carried out in rich medium (e.g. LB). The plasmid pSK-PgapA-GRE2p was then introduced into the strain obtained E. coli [Δ(udhA, qor, pgi, edd)] (Example 3) by electroporation, and the resulting strain E. coli [Δ(udhA, qor, pgi, edd) pSK-PgapA-GRE2p] was selected on rich medium.

The strain obtained E. coli [Δ(udhA, qor, pgi, edd) pSK-PgapA-GRE2p] was then grown in a minimum medium containing glucose and ethylacetoacetate. A strain E. coli [pSK-PgapA-GRE2p] was grown under the same conditions.

When growth was completed the following variables were compared:
  The time course of the biomass of each strain during the bioconversion phase.
  The quantity of ethyl-3-hydroxybutyrate produced in the extracellular medium.
  The quantity of ethyl-3-hydroxybutyrate accumulated in the cells.
  The productivity in terms of ethyl-3-hydroxybutyrate.
  The yield glucose/ethyl-3-hydroxybutyrate.

We observed that the strain E. coli [Δ(udhA, qor, pgi, edd) pSK-PgapA-GRE2p] gave a greater production yield of ethyl-3-hydroxybutyrate than the non-optimized strain.

EXAMPLE 6

Construction of the Strain E. coli [Δ(udhA, qor, pfkA, pfkB) pSK-PgapA-GRE2p] and Bioconversion of Ethylacetoacetate into ethyl-3-hydroxybutyrate The inactivation of the genes pfkA and pfkB was carried out in the strain E. coli [Δ(udhA, qor)] (Example 2) using the method described in Example 2 and the following oligonucleotides:

```
DpfkAF
ggt gtg ttg aca agc ggc ggt gat gcg cca ggc atg
aac gcc gca att cgc ggg gtt gtt cgt tct gcg ctg
aca gaa ggTGTAGGCTGGAGCTGCTTCG
```

-continued

DpfkAR
Ttcgcgcagtccagccagtcacctttgaacggacgcttcatgttttcgat
agcgtcgatgatgtcgtggtgaaccagctgCATATGAATATCCTCCTTAG PfkAF
Cgcacgcggcagtcagggccgacccgc PfkAR
ccctacgcoccacttgttcatcgcccg DpfkBF (1804421-1804499)
gcgccctctctcgatagcgcaacaattaccccgcaaatttatcccgaagg
aaaactgcgctgtaccgcaccggtgttcgTGTAGGCTGGAGCTGCTTCG DpfkBR (1805320-1805241)
gcgggaaaggtaagcgtaaatttttgcgtatcgtcatgggagcacagac
gtgttccctgattgagtgtggctgcactccCATATGAATATCCTCCTTAG PfkBF (1803996-1804025)
tggcaggatcatccatgacagtaaaaacgg PfkBR (1805657-1805632)
gccggttgcactttgggtaagccccg The construction was carried out in rich medium (e.g. LB). The plasmid pSK-PgapA-GRE2p was then introduced into the strain obtained E. coli [Δ(udhA, qor, pfkA, pfkB)] (Example 3) by electroporation, and the resulting strain E. coli [Δ(udhA, qor, pfkA, pfkB) pSK-PgapA-GRE2p] was selected on rich medium.

The strain obtained E. coli [Δ(udhA, qor, pfkA, pfkB) pSK-PgapA-GRE2p] was then grown in minimum medium containing glucose and ethylacetoacetate. A strain E. coli [pSK-PgapA-GRE2p] was grown under the same conditions.

When growth was completed the following variables were compared:
The time course of the biomass of each strain during the bioconversion phase.
The quantity of ethyl-3-hydroxybutyrate produced in the extracellular medium.
The quantity of ethyl-3-hydroxybutyrate accumulated in the cells.
The productivity in terms of ethyl-3-hydroxybutyrate.
The yield glucose/ethyl-3-hydroxybutyrate.

We observed that the strain E. coli [Δ(udhA, qor, pfkA, pfkB) pSK-PgapA-GRE2p] gave a greater production yield of ethyl-3-hydroxybutyrate than the non-optimized strain.

|  | $mol_{EHB}/mol_{Glucose}$ |
| --- | --- |
| MG1655 pSK-PgapA-GRE2p | 0.75 |
| MG1655 Δ(udhA, qor, pfkA, pfkB) pSK-PgapA-GRE2p | 3.46 |

EXAMPLE 7

Construction of the Strain E. coli [Δ(udhA, qor, pgi, lpd) plpd*, pSK-PgapA-GRE2p] and Bioconversion of Ethylacetoacetate into ethyl-3-hydroxybutyrate The gene lpd coding for NAD-dependent dihydrolipoamide dehydrogenase involved in the multienzyme complex pyruvate dehydrogenase was deleted using the method described in Example 2, except that the initial strain was the strain E. coli [Δ(udhA, qor, pgi)] described in Example 4 instead of being a wild strain. The construction and the selection of the modified strain were carried out in rich medium (e.g. LB). The strain obtained was E.coli [Δ(udhA, qor, pgi, lpd)].

In addition, the plasmid p-lpd* was constructed, which allows the overexpression of a NADP-dependent dihydrolipoamide dehydrogenase. There are various possible ways to modify the cofactor specificity of an enzyme. For example, Bocanegra et al. (1993) report a method to create a NADP-dependent dihydrolipoamide dehydrogenase.

The plasmids p-lpd* and pSK-PgapA-GRE2p were then introduced by electroporation into the strain E. coli [Δ(udhA, qor, pgi, lpd)]. Alternatively, lpd* could be cloned on pSK-PgapA-GRE2p, giving the plasmid pSK-PgapA-GRE2p-lpd* then introduced by electroporation into the strain E. coli [Δ(udhA, qor, pgi, lpd)]. The construction and the selection of the modified strain were carried out in rich medium (e.g. LB).

The strain E. coli [Δ(udhA, qor, pgi, lpd) pSK-PgapA-GRE2p, p-lpd*)] obtained was then grown in minimum medium containing glucose and ethylacetoacetate. A strain E. coli [pSK-PgapA-GRE2p] was grown under the same conditions.

When growth was completed the following variables were compared:
The time course of the biomass of each strain during the bioconversion phase.
The quantity of ethyl-3-hydroxybutyrate produced in the extracellular medium.
The quantity of ethyl-3-hydroxybutyrate accumulated in the cells.
The productivity in terms of ethyl-3-hydroxybutyrate.
The yield glucose/ethyl-3-hydroxybutyrate.

We observed that the strain E. coli [Δ(udhA, qor, pgi, lpd) pSK-PgapA-GRE2p, p-lpd*)] gave a greater production yield of ethyl-3-hydroxybutyrate than the non-optimized strain.

EXAMPLE 8

Construction of the Plasmid pRSGK-GRE2p

The plasmid pYGK was constructed by insertion of the promoter Ppgk, the multicloning site and the terminator cyc1 of the vector pYPG2 in the vector pBluescript-SK (pSK). To do this, the promoter Ppgk, the multicloning site and the terminator cyc1 were amplified with polymerase Pfu Turbo from the vector pYPG2. The PCR product obtained was then digested by restriction enzymes SacII-NotI and ligated to the vector pSK digested by the restriction enzymes ApaI-SmaI, ligated and digested by the restriction enzymes NotI-SacII, and dephosphorylated to give the plasmid pYGK.

The plasmid pYGK was then introduced into the strain E. coli DH5α to verify the construction. The sequencing of the promoter Ppgk, the multicloning site and the terminator cyc1 of the plasmid pYGK with the oligonucleotides universal M13 reverse and universal M13 forward was then carried out to confirm the construction.

The plasmid pYGK-GRE2p was then constructed by insertion of the gene GRE2p in the plasmid pYGK. To do this, the gene GRE2p of Saccharomyces cerevisiae was amplified with the polymerase Pwo from chromosomal DNA, using the following oligonucleotides:

Ome376_Gre2 pYGK F (SmaI)
Acgtacgtccccgggaaaaatgtcagttttcgtttcaggtgc

Ome377_Gre2 pYGK R (ApaI)
ACGTACGGGCCCTTATATTCTGCCCTCAAATTTTAAAATTTGGG

The PCR product obtained was then digested by the restriction enzymes ApaI-SmaI and ligated to the vector pYGK digested by the restriction enzymes ApaI-SmaI and dephosphorylated to give the plasmid pYGK-GRE2p.

The plasmid pYGK-GRE2p was then introduced into the strain *E. coli* DH5α to verify the construction. The sequencing of the gene GRE2p of the plasmid pYGK-GRE2p with the oligonucleotides universal M13 reverse and universal M13 forward was then carried out to confirm the construction.

The plasmid pRSGK-GRE2p was finally obtained by digestion of the plasmids pYGK-GRE2p and pRS426 with the restriction enzymes NotI-SacII followed by ligation.

EXAMPLE 9

Construction of the Strain *S. cerevisiae* [Δ(ZTA1) pRSGK-GRE2p] and Bioconversion of Ethylacetoacetate into ethyl-3-hydroxybutyrate The inactivation of the gene ZTA1 was carried out by inserting a marker (antibiotic resistance, auxotrophy) while at the same time deleting most of the gene concerned. The technique used is described by Brachmann et al. (Designer deletion strains derived from *Saccharomyces cerevisae* S288C: a useful set of strains and plasmids for PCR-mediated gene disruption and other applications, Yeast, 1998, 14: 115-32). It is also possible to use the method described by Wach et al. (New heterologous modules for classical or PCR-based gene disruptions in *Saccharomyces cerevisiae*, Yeast, 1994, 10: 1793-1808).

In all cases a final strain of *S. cerevisiae* [Δ(ZTA1)] was obtained into which the plasmid pRSGK-GRE2p (Example 8) was then introduced.

Alternatively, it was also possible to introduce the plasmid pRSGK-GRE2p into an available Δ(ZTA1) strain, for example the strain EUROSCARF Y33183 (genotype: BY4743; Mat a/α; his3D1/his3D1; leu2D0/leu2D0; lys2D0/LYS2; MET15/met15D0; ura3D0/ura3D0; YBR046c::kanMX4/YBR046c::kanMX4). It was then possible, after sporulation, to recover a homozygote strain of *S. cerevisiae* [Δ(ZTA1) pRSGK-GRE2p].

The strain *S. cerevisiae* [Δ(ZTA1) pRSGK-GRE2p] obtained was then grown in a minimum medium containing glucose and ethylacetoacetate.

The control strain *S. cerevisiae* [pRSGK-GRE2p] was grown under the same conditions.

When growth was completed the following variables were compared:
  The time course of the biomass of each strain during the bioconversion phase.
  The quantity of ethyl-3-hydroxybutyrate produced in the extracellular medium.
  The quantity of ethyl-3-hydroxybutyrate accumulated in the cells.
  The productivity in terms of ethyl-3-hydroxybutyrate.
  The yield glucose/ethyl-3-hydroxybutyrate.

We found that the strain *S. cerevisiae* [Δ(ZTA1) pRSGK-GRE2p] gave a higher production yield of ethyl-3-hydroxybutyrate than the non-optimized strain.

EXAMPLE 10

Construction of the Strain *S. cerevisiae* [Δ(ZTA1, PGI1) pRSGK-GRE2p] and Bioconversion of Ethylacetoacetate into ethyl-3-hydroxybutyrate The inactivation of the gene PGI1 was carried out in the strain *S. cerevisiae* [Δ(ZTA1) pRSGK-GRE2p] using the method described in Example 9, and the following oligonucleotides:

```
Dpgi1F
CCAACGCAGACCGCTGCCTGGCAGGCACTACAGAAACACTTCGATGAAAT
GAAAGACGTTACGATCGCCGATCTTTTTGCTGTAGGCTGGAGCTGCTTCG Dpgi1R
GCGCCACGCTTTATAGCGGTTAATCAGACCATTGGTCGAGCTATCGTGGC
TGCTGATTTCTTTATCATCTTTCAGCTCTGCATATGAATATCCTCCTTAG Pgi1F
GCGGGGCGGTTGTCAACGATGGGGTCATGC Pgi1R
CGGTATGATTTCCGTTAAATTACAGACAAG
```

Alternatively it was possible to use an available Δ(PGI1) strain, for example the strain EUROSCARF Y23336 (Mat α/a; his3D1/his3D1; leu2D0/leu2D0; lys2D0/LYS2; MET15/met15D0; ura3D0/ura3D0; YBR196c::kanMX4/YBR196c). The strain was then converted by the plasmid pRSGK-GRE2p (Example 8), and the deletion of the gene ZTA1 was then carried out using the method described in Example 9.

The strain *S. cerevisiae* [Δ(ZTA1, PGI1) pRSGK-GRE2p] obtained was then grown in minimal medium containing glucose and ethylacetoacetate.

The control strain *S. cerevisiae* [pRSGK-GRE2p] was grown in the same conditions.

When growth was completed the following variables were compared:
  The time course of the biomass of each strain during the bioconversion phase.
  The quantity of ethyl-3-hydroxybutyrate produced in the extracellular medium.
  The quantity of ethyl-3-hydroxybutyrate accumulated in the cells.
  The productivity in terms of ethyl-3-hydroxybutyrate.
  The yield glucose/ethyl-3-hydroxybutyrate.

We observed that the strain *E. coli* [Δ(ZTA1, PGI1) pRSGK-GRE2p] gave a higher production yield of ethyl-3-hydroxybutyrate than the non-optimized strain.

EXAMPLE 11

Construction of the Strain *S. cerevisiae* [Δ(ZTA1, PFK1, PFK2) pRSGK-GRE2p] and Bioconversion of Ethylacetoacetate into ethyl-3-hydroxybutyrate The genes PFK1 and PFK2 were deleted in the strain *S. cerevisiae* [Δ(ZTA1)] using the method described in Example 9, and the following oligonucleotides:

```
Dpfk1F
ATGCAATCTCAAGATTCATGCTACGGTGTTGCATTCAGATCTATCATCAC
AAATGATGAAAAGCTTCGTACGCTGCAGGTCG Dpfk1R
TTTGTTTTCAGCGGCTAAAGCGGCTACCTCAGCTCTCAACTTTAATCTAC
CGGACAGGATGGGCCACTAGTGGATCTGATATC Pfk1 int F
GCTTTCTTAGAAGCTACCTCCG Pfk1 int R
GAACCGACAAGACCAACAATGG Pfk2 int F
CAGTTGTACACTTTGGACCC Pfk2 int R
GATCAGCACCAGTCAAAGAACC
```

The strain was then converted by the plasmid pRSGK-GRE2p (Example 8).

The strain *S. cerevisiae* [Δ(ZTA1, PFK1, PFK2) pRSGK-GRE2p] obtained was then grown in minimum medium containing glucose and ethylacetoacetate.

The control strain *S. cerevisiae* [pRSGK-GRE2p] was grown under the same conditions.

When growth was completed the following variables were compared:

The time course of the biomass of each strain during the bioconversion phase.
The quantity of ethyl-3-hydroxybutyrate produced in the extracellular medium.
The quantity of ethyl-3-hydroxybutyrate accumulated in the cells.
The productivity in terms of ethyl-3-hydroxybutyrate.
The yield glucose/ethyl-3-hydroxybutyrate.

We observed that the strain *S. cerevisiae* [Δ(ZTA1, PFK1, PFK2) pRSGK-GRE2p] gave a higher production yield of ethyl-3-hydroxybutyrate than the non-optimized strain.

| | $mol_{EHB}/mol_{Glucose}$ |
|---|---|
| *S. cerevisiae* [pRSGK-GRE2p] | in progress |
| *S. cerevisiae* [Δ(ZTA1, PFK1, PFK2) pRSGK-GRE2p] | in progress |

EXAMPLE 12

Comparison Between Experimental Values and Predictions Using the Metabolic Model for the Optimization of the Production of ethyl-3-hydroxybutyrate by *Escherichia coli*

We found a close correlation between predictive modelling (Example 1) and the experimental results described in Examples 3, 4, 5, 6, 7, 9, 10 and 11.

Examples 1 to 11 above are specific applications of the patent and do not restrict its scope. Those skilled in the art can readily adapt these examples for the biotransformation of substances formed by a NADPH-dependent synthesis. The algorithm MetOpt® and the strategy for optimizing a NADPH-dependent biotransformation process via the optimization of the NADPH/NADP+ ratio is validated; this patent thus claims an application covering all NADPH-dependent biotransformations that can be modelled and predicted with MetOpt®, or any of its derivatives, using *E. coli*, *S. cerevisiae* or any other microorganism.

EXAMPLE 13

Calculation of Theoretical Optimal Yields in Fermentation Processes in *E. coli*

Example 12 shows that the models MetOpt® developed by the Company are applicable to the bioconversions and should be more generally applicable to biotransformations such as fermentations.

For example, MetOpt®-Coli model was applied to the production of cysteine or 3-hydroxypropionate by the fermentation of glucose in the strains of *E. coli* optimized according to the invention. The parameters used were the same as in Example 1, namely: 1) a glucose import flux of 3 $mmol \cdot g^{-1} \cdot h^{-1}$, 2) a variable growth rate of 0, 0.15 and 0.25 $h^{-1}$, 3) a variable membrane-bound transhydrogenase flux (pntAB) less than or equal to 1 $mmol \cdot g^{-1} \cdot h^{-1}$; the limiting value of membrane-bound transhydrogenase flux was determined from the literature (Hanson, 1979; Anderlund et al., 1999; Emmerling et al., 2002), and 4) maintenance flux limited to between 5 and 22 $mmol \cdot g^{-1} \cdot h^{-1}$.

a) Case of Production of Cysteine by Fermentation of Glucose

| | $\mu = 0$ | $\mu = 0.15\ h^{-1}$ | $\mu = 0.25\ h^{-1}$ |
|---|---|---|---|
| Δ(udhA, qor, pgi) | 0.66 | 0.37 | 0.09 |
| Δ(udhA, qor, pgi) gapA-NADP-dependent | 0.78 | 0.37 | 0.09 |
| Δ(udhA, qor, pgi) lpd-NADP-dependent | 0.78 | 0.37 | 0.09 |
| Δ(udhA, qor, pgi) gapA-NADP-dependent lpd-NADP-dependent | 0.78 | 0.37 | 0.09 |
| Δ(udhA, qor, pfkA, pfkB) | 0.40 | 0.18 | 0.01 |
| Δ(udhA, qor, pfkA, pfkB) gapA-NADP-dependent | 0.62 | 0.30 | 0.06 |
| Δ(udhA, qor, pfkA, pfkB) lpd-NADP-dependent | 0.71 | 0.36 | 0.13 |
| Δ(udhA, qor, pfkA, pfkB) gapA-NADP-dependent lpd-NADP-dependent | 0.77 | 0.42 | 0.17 |

Theoretical Optimal Yields for the Production of Cysteine by Strains of *E. coli* Optimized for NADP+ Reduction Capacity (mol per mol of Glucose)

To further improve the theoretical optimal yield of the strains optimized according to the invention additional modifications can be made, such as the overexpression of at least one gene that can be zwf, gnd, pntA, pntB or icd and/or the deletion of at least one gene that can be edd, aceA, aceB or aceK.

In practice, to obtain such yields other modifications have to be made to the strains optimized according to the invention, for example by overexpressing the gene cysB as described in the patent WO0127307, or by modifying the gene cysE as described in the patent EP0885962.

b) Case of Production of 3-hydroxypropionate by Fermentation of Glucose

The production of 3-hydroxypropionate was carried out in strains of *E. coli* containing the genes coding for the enzymes of the 3-hydroxypropionate synthesis pathway, for example the malonyl-coA reductase of *Chloroflexus aurantiacus* (Hugler et al., *Journal of Bacteriology*, 2002, 184: 2404-2410).

| | $\mu = 0$ | $\mu = 0.15\ h^{-1}$ | $\mu = 0.25\ h^{-1}$ |
|---|---|---|---|
| Δ(udhA, qor, pgi) | 1.33 | 0.79 | 0.30 |
| Δ(udhA, qor, pgi) gapA-NADP-dependent | 1.76 | 0.99 | 0.30 |
| Δ(udhA, qor, pgi) lpd-NADP-dependent | 1.82 | 0.99 | 0.30 |
| Δ(udhA, qor, pgi) gapA-NADP-dependent lpd-NADP-dependent | 1.82 | 0.99 | 0.30 |

| | $\mu = 0$ | $\mu = 0.15\ h^{-1}$ | $\mu = 0.25\ h^{-1}$ |
|---|---|---|---|
| Δ(udhA, qor, pfkA, pfkB) | 1.62 | 0.66 | 0.03 |
| Δ(udhA, qor, pfkB) gapA-NADP-dependent | 1.76 | 0.79 | 0.07 |
| Δ(udhA, qor, pfkA, pfkB) lpd-NADP-dependent | 1.79 | 0.84 | 0.07 |
| Δ(udhA, qor, pfkA, pfkB) gapA-NADP-dependent lpd-NADP-dependent | 1.79 | 0.84 | 0.07 |

Theoretical Optimal Yields for the Production of 3-hydroxypropionate by Strains of *E. coli* Optimized for NADP+ Reduction Capacity (mol per mol of Glucose)

To further improve the theoretical optimal yield of the strains optimized according to the invention, additional modifications can be made, such as the overexpression of at least one gene that can be zwf, gnd, pntA, pntB or icd and/or the deletion of at least one gene that can be edd, aceA, aceB or aceK.

EXAMPLE 14

Calculation of Theoretical Optimal Yields in Fermentation Processes in *S. cerevisiae*; Application to the Production of Hydrocortisone Example 12 shows that the MetOpt® models developed by the Company are applicable to bioconversions and should be more generally applicable to biotransformations such as fermentations.

For example, the MetOpt®-Scere model was applied to the production of hydrocortisone by fermentation of glucose in the strains of *S. cerevisiae* optimized according to the invention. The parameters used were the same as in Example 1, namely: 1) a glucose import flux of 3 mmol·g$^{-1}$·h$^{-1}$, 2) a variable growth rate of 0, 0.15 and 0.25 h$^{-1}$, 3) a maintenance flux less than or equal to 22 mmol·g$^{-1}$·h$^{-1}$, 4) reactions of aldehyde dehydrogenases (ALD2, ALD3, ALD6) irreversible and set in the direction acetate+NAD(P)H→acetaldehyde+ NAD(P), and 5) no activities equivalent to udhA or pntA,B.

The model allows for mitochondrial and peroxisomal compartmentalization.

This representation of the results demonstrates the real contribution made by each of the mutations made according to the invention to the improvement in NADPH production and so to the improvement in the hydrocortisone production flux.

The production of hydrocortisone was achieved in strains of *S. cerevisiae* containing genes coding for enzymes of the hydrocortisone synthesis pathway (Szczebara et al., 2003, *Nature Biotechnology*, 21: 143-149).

| | $\mu = 0$ | $\mu = 0.15\ h^{-1}$ | $\mu = 0.25\ h^{-1}$ |
|---|---|---|---|
| Δ(ZTA1, PGI1) | 0.12 | 0.08 | 0.06 |
| Δ(ZTA1, PGI1) TDH1,2,3-NADP-dependent | 0.21 | 0.14 | 0.10 |
| Δ(ZTA1, PGI1) LPD1-NADP-dependent | 0.20 | 0.14 | 0.10 |
| Δ(ZTA1, PGI1) TDH1,2,3-NADP-dependent LPD1-NADP-dependent | 0.21 | 0.14 | 0.10 |

Theoretical Optimal Yields for the Production of Hydrocortisone by Strains of *E. coli* Optimized for NADP+ Reduction Capacity (mol per mol of Glucose)

The strains from which the genes PFK1 and PFK2 have been deleted are unable to produce hydrocortisone, and may not even be viable. This is because the production of hydrocortisone is limited more by carbon demand than by NADPH requirement. One solution is to allow a weak expression of a transhydrogenase type activity in the yeast. However, modelling shows that the hydrocortisone production will never be as high as when the PGI1 gene is deleted.

To further improve the theoretical optimum yield of the strains optimized according to the invention, additional modifications can be made, such as the overexpression of at least one gene that can be ZWF, SOL1, SOL2, SOL3, SOL4, GND1, GND2, IDP1, IDP2 or IDP3, and/or the deletion of at least one gene that can be either ICL1 or DAL7.

REFERENCES

Anderson, E. H. (1946) Growth requirements of virus-resistant mutants of *Escherichia coli* strain "B", *Proc. Natl. Acad. Sci. USA* 32:120-128

Baudin, A.; Ozier-Kalogeropoulos, O.; Denouel, A.; Lacroute, F. and Cullin, C. (1993) A simple and efficient method for direct gene deletion in *Saccharomyces cerevisiae*, *Nucl. Acids Res.* 21, 3329-3330

Bocanegra, J. A. Scrutton, N. S.; Perham, R. N. (1993) Creation of an NADP-dependent pyruvate dehydrogenase multienzyme complex by protein engineering. *Biochemistry* 32: 2737-2740

Brachmann C B, Davies A, Cost G J, Caputo E, Li J, Hieter P, Boeke J D. (1998) Designer deletion strains derived from *Saccharomyces cerevisiae* S288C: a useful set of strains and plasmids for PCR-mediated gene disruption and other applications. *Yeast*. 14:115-32.

Datsenko, K. A.; Wanner, B. L. (2000) One-step inactivation of chromosomal genes in *Escherichia coli* K-12 using PCR products. *Proc. Natl. Acad. Sci. USA* 97: 6640-6645

Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.

Sambrook et al. (1989 Molecular cloning: a laboratory manual. 2$^{nd}$ Ed. Cold Spring Harbor Lab., Cold Spring Harbor, N.Y.

Schaefer U.; Boos, W.; Takors, R.; Weuster-Botz, D. (1999) Automated sampling device for monitoring intracellular metabolite dynamics, *Anal. Biochem.* 270: 88-96

Wach, A.; Brachat, A.; Pohlmann, R.; and Philippsen, P. (1994) New heterologous modules for classical or PCR-based gene disruptions in *Saccharomyces cerevisiae*, *Yeast* 10, 1793-1808, 1994.

The invention claimed is:

1. A strain of a micro-organism comprising NADPH-oxidizing activity that is reduced by a deletion of at least one gene coding for an enzyme selected from the group consisting of a quinone oxidoreductase and a soluble transhydrogenase, and wherein said strain has undergone a modification that enhances at least one NADP+-reducing enzyme activity of said strain by a deletion of at least one gene coding for an enzyme selected from the group consisting of a phosphoglucose isomerase and a phosphofructokinase.

2. A strain according to claim 1, wherein said strain further comprises a modification of at least one gene coding for an enzyme selected from the group consisting of a dihydrolipoamide dehydrogenase and a glyceraldehyde 3-phosphate dehydrogenase.

3. A strain according to claim 1, wherein said strain further comprises overexpression of at least one gene coding for an enzyme selected from the group consisting of a glucose 6-phosphate dehydrogenase, a 6-phosphogluconolactonase, a 6-phosphogluconate dehydrogenase, an isocitrate dehydrogenase, and a membrane-bound transhydrogenase.

4. A strain according to claim 1, wherein said strain further comprises a modification of at least one gene coding for an enzyme selected from the group consisting of a 6-phosphogluconate dehydratase, a malate synthase, an isocitrate lyase, and an isocitrate dehydrogenase kinase/phosphatase.

5. A strain according to claim 1, wherein said strain further comprises at least one endogenous or exogenous gene coding for an enzyme involved in the biotransformation of a substance of interest.

6. A strain according to claim 1, wherein said strain further comprises at least one selection marker gene.

7. A strain according to claim 1, wherein said strain is selected from the group consisting of *Aspergillus* sp., *Bacillus* sp., *Brevibacterium* sp., *Clostridium* sp., *Corynebacterium* sp., *Escherichia* sp., *Gluconobacter* sp., *Penicillium* sp., *Pichia* sp., *Pseudomonas* sp., *Rhodococcus* sp., *Saccharomyces* sp., *Streptomyces* sp., *Xanthomonas* sp, and *Candida* sp.

8. A method for the preparation of the strain of claim 1 comprising:
(a) deleting at least one gene coding for an enzyme selected from the group consisting of a quinone oxidoreductase and a soluble transhydrogenase, and (b) deleting at least one gene coding for an enzyme selected from the group consisting of a phosphoglucose isomerase, a phosphofructokinase, a 6-phosphogluconate dehydratase, a malate synthase, an isocitrate lyase and an isocitrate dehydrogenase kinase/phosphatase, and (c) optionally modifying at least one gene coding for an enzyme selected from the group consisting of at least one of a dihydrolipoamide dehydrogenase and a glyceraldehyde 3-phosphate dehydrogenase, and (d) optionally overexpressing at least one gene coding for an enzyme selected from the group consisting of a glucose 6-phosphate dehydrogenase, a 6-phosphogluconolactonase, a 6-phosphogluconate dehydrogenase, an isocitrate dehydrogenase, and a membrane transhydrogenase.

9. A method for the production of a substance of interest formed by a biosynthesis route of which at least one step is NADPH-dependent comprising:
growing micro-organisms of the strain of claim 1 in an appropriate culture medium that favours their growth and contains substances necessary for carrying out biotransformations by fermentation or bioconversion, except NADPH; and
b) extracting a substance of interest from the medium and optionally purifying said substance.

10. The method according to claim 9, wherein said substance of interest is an amino acid, or a vitamin, or a sterol, or a flavonoid, or a fatty acid, or an organic acid, or a polyol or a hydroxyester.

11. The method according to claim 10, wherein said substance of interest is an amino acid.

12. A strain according to claim 1, wherein said NADPH-oxidizing activity is reduced by a deletion of at least one gene coding for a quinone oxidoreductase and at least one gene coding for a soluble transhydrogenase.

13. A strain according to claim 1, wherein said strain has undergone a modification that enhances at least one NADP+-reducing enzyme activity of said strain by a deletion of at least one gene coding for a phosphoglucose isomerase and at least one gene coding for a phosphofructokinase.

* * * * *